United States Patent [19]

Lundsgaard

[11] Patent Number: 4,997,769
[45] Date of Patent: Mar. 5, 1991

[54] METHOD AND AN APPARATUS FOR DETERMINING BLOOD COMPONENTS

[75] Inventor: Finn C. Lundsgaard, Tastrup, Denmark

[73] Assignee: Radiometer A/S, Denmark

[21] Appl. No.: 512,038

[22] Filed: Apr. 13, 1990

Related U.S. Application Data

[63] Continuation of Ser. No. 188,172, Apr. 26, 1988, abandoned, which is a continuation of Ser. No. 63,801, Jun. 23, 1987, abandoned, which is a continuation of Ser. No. 876,939, Jun. 20, 1986, abandoned.

[30] Foreign Application Priority Data

Jun. 21, 1985 [DK] Denmark ............................ 2820/85

[51] Int. Cl.$^5$ ...................... G01N 15/05; G01N 33/49
[52] U.S. Cl. ........................................ 436/66; 356/39;
356/40; 356/41; 422/67; 422/82.09; 422/73;
422/81; 436/47; 436/67
[58] Field of Search ............... 436/47, 67, 66; 422/67,
422/82.09, 73, 81; 356/39, 40, 41

[56] References Cited

U.S. PATENT DOCUMENTS

| | | | |
|---|---|---|---|
| 3,874,850 | 4/1975 | Sorensen et al. | 422/81 X |
| 3,922,088 | 11/1975 | Lübbers et al. | 356/40 |
| 3,923,397 | 12/1975 | Shuck | 356/39 |
| 3,930,726 | 1/1976 | Dolive | 356/39 |
| 4,013,417 | 3/1977 | Raffaele | 436/66 X |
| 4,324,556 | 4/1982 | Robertson et al. | 356/40 X |
| 4,502,786 | 3/1985 | Golias et al. | 356/40 X |

OTHER PUBLICATIONS

Critical Care Medicine, vol. 12, No. 10, Oct. 1984, pp. 907–909, "Effect of Intralipid on Measurements of Total Hemoglobin and Oxyhemoglobin in Whole Blood".
The Acid-Base Status of Blood, Ole Siggard-Andersen, 4th Ed. (1974), pp. 183–187.
Textbook of Clinical Chemistry, N. W. Tietz, Ph.D., pp. 1555–1561 (1986).
Van Kampen et al., Advanced Clinical Chemistry, 8, pp. 141–187 (1965), "Determination of Hemoglobin and its Derivatives".
Journal of Applied Physiology, 13, pp. 147–152 (1958), "A Simplified Lucite Cuvette for the Spectrophotometric Measurement of Hemoglobin and Oxyhemoglobin".

Primary Examiner—Robert J. Warden
Assistant Examiner—Jill Johnston
Attorney, Agent, or Firm—Bryan, Cave, McPheeters & McRoberts

[57] ABSTRACT

Method and apparatus for spectrophotometrically determining the concentration of a number of hemoglobin derivatives comprising at least deoxyhemoglobin and oxyhemoglobin or parameters derived from the concentration of individual hemoglobin derivatives, in particular the oxygen saturation fraction, in whole blood, in which light is transmitted to the blood under test, the modification on the light transmitted to the blood which the blood causes is determined at a number of individual wavelengths, and the concentrations (or the derived parameters) are determined on the basis of the light modification at the individual wavelengths and on the basis of predetermined coefficients representing the light absorption characteristics of each of the hemoglobin derivatives at each of the individual wavelengths, any error on the determination values due to turbidity being substantially compensated for by utilizing predetermined coefficients representing an absorption characteristic of turbidity at each of the wavelengths. The measurement is normally performed at a number of wavelengths which is at least equal to the number of hemoglobin derivatives to be determined plus one. Although the turbidity-caused contribution to the total reduction in the light transmission is not based on any direct proportionality between the reduction in light transmission and the concentration of the turbidity-causing components (such as is the case with the hemoglobin derivatives), the "absorbances" caused by the turbidity at each particular wavelength may simply be eliminated from the equation set from which the concentrations of the hemoglobin derivatives are calculated.

31 Claims, 5 Drawing Sheets

METHOD AND AN APPARATUS FOR DETERMINING BLOOD COMPONENTS

This is a continuation of U.S. application Ser. No. 07/188,172, filed Apr. 26, 1988, now abandoned, which is a continuation of U.S. application Ser. No. 07/063,801 filed Jun. 23, 1987, now abandoned, which is a continuation of U.S. application Ser. No. 06/876,939 filed Jun. 20, 1986, now abandoned.

TECHNICAL BACKGROUND

The present invention relates to a method and an apparatus for spectrophotometrically determining the concentration of a number of hemoglobin derivatives (or parameters derived from the concentration of individual hemoglobin derivatives) in whole blood.

It is known to determine the concentration of various hemoglobin derivatives such as deoxyhemoglobin, oxyhemoglobin, carboxyhemoglobin, methemoglobin, and sulfhemoglobin by spectrophotometric methods (cf. e.g., Ole Siggaard-Andersen, *The Acid-Base Status of the Blood*, 4th edition, Munksgaard, Copenhagen, 1974, pp. 181-187, and U.S. Pat. No. 3,927,614). Information concerning the concentration of the various hemoglobin derivatives, in particular oxyhemoglobin and deoxyhemoglobin, is important in addition to information on the oxygen concentration or oxygen partial pressure of the blood in several clinical situations such as, e.g., when a patient is under anaesthesia.

As explained in Siggaard-Andersen, loc.cit., the theoretical basis for the spectrophotometric determination of the concentration of hemoglobin derivatives in a mixture is that the total absorbance at any wavelength is the sum of the contribution of each derivative, and that each derivative obeys Lambert-Beer's law. Thus, $$A^\lambda = l \cdot \Sigma \epsilon_y^\lambda \cdot C_y$$

wherein $A^\lambda$ is the absorbance of the mixture at the wavelength $\lambda$, $C_y$ is the concentration of derivative y, l is the light path length, and $\epsilon_y^\lambda$ is the extinction coefficient of derivative y at wavelength $\lambda$.

The absorbance A is defined as $$A = \log \frac{lo}{l}$$

wherein lo is the intensity of the incident light on the sample, and l is the intensity of the resultant modified light. The ratio l/lo is designated the transmittance.

In accordance with this, the concentrations of a certain number of hemoglobin derivatives in a blood sample may be determined by measuring the transmittance or the absorbance of the blood sample at at least the same number of different wavelengths. Provided that the path length of the light and data representative of the extinction coefficient for each derivative at each wavelength are known, the unknown concentrations may be determined by solving an equation set of the certain number of linear equations with the same number of variables.

While the known methods for determining hemoglobin derivatives (e.g. the methods described in U.S. Pat. No. 3,972,614) function satisfactorily on most blood samples, wrong results will be obtained when using these methods in connection with turbidity-containing blood samples. Thus, Siggaard-Andersen, loc.cit., pp. 186-187, mentions that turbidity of the hemolyzate, caused by leukocytes, lipemia, or erythrocyte ghosts, is a major source of error. A recent article, "Effect of Intralipid on Measurements of Total Hemoglobin and Oxyhemoglobin in Whole Blood" Lakshman R. Sehgal et al., *Critical Care Medicine*, Vol. 12, 10, October 1984, pp. 907-909 deals with the problems incurred by the light scattering effect on the determination of hemoglobin species on blood from patients who have received Intralipid ® (an infusion liquid containing, inter alia, soy lecithin and glycerol). The article states that the light scattering affects the measured concentrations of all hemoglobin species, but most dramatically the methemoglobin, and concludes that the data for hemoglobin derivatives measured on blood samples from patients who have received Intralipid ® should be disregarded.

Thus, the presence of turbidity in blood subjected to hemoglobin derivative determination presents a major problem which has, until now, not been solved in a satisfactory manner.

It has now been found that the error derived from the existence of turbidity in whole blood under test can be eliminated to a completely satisfactory degree, thereby making it possible to obtain reliable data for the concentration of the various hemoglobin derivatives irrespective of whether the blood in question contains turbidity-incurring components or not.

DISCLOSURE OF THE INVENTION

The invention relates to a method for spectrophotometrically determining the concentration of a number of hemoglobin derivatives comprising at least deoxyhemoglobin and oxyhemoglobin or parameters derived from the concentration of individual hemoglobin derivatives, in particular the oxygen saturation fraction, in whole blood, comprising transmitting light to the blood under test, determining the modification caused by the blood on the light transmitted to the blood at a number of individual wavelengths, and determining the concentrations (or the derived parameters) on the basis of the light modification at the individual wavelengths and on the basis of predetermined coefficients representing the light absorption characteristics of each of the hemoglobin derivatives at each of the individual wavelengths, any error on the determination values due to turbidity being substantially compensated for by utilizing predetermined coefficients representing an absorption characteristic of turbidity at each of the wavelengths.

The invention is based on the finding that it is possible to treat the determination of the turbidity-caused contribution to the total reduction in light transmission in the same manner as the determination of the reduction caused by each of the individual hemoglobin derivatives, in other words, to treat the contribution from the turbidity at each wavelength at which measurement is made analogously to the contribution from each hemoglobin derivative. Although there is, in the case of turbidity, no direct proportionality between the reduction in light transmission caused thereby at each particular wavelength and the concentration of the turbidity-causing components, this is not of critical disadvantage, as the "absorbances" caused by turbidity at each particular wavelength may simply be eliminated from the equation set, thereby rendering it insignificant that the "absorbance" derived from a turbidity at each particular wavelength cannot in any simple manner be correlated to the concentration of the turbidity-causing components. What is of importance to the present invention is that a "concentration of turbidity" can be determined and thereafter used for the compensation, irrespective of what was the actual concentration of the various turbidity-causing components.

The above-mentioned parameters derived from the concentration of individual hemoglobin derivatives may be the parameters often used in practice for evaluating the hemoglobin derivative distribution, such as tHb (total hemoglobin), $HbO_2$ (fraction of oxyhemoglobin), HbCO (fraction of carboxyhemoglobin), MetHb (fraction of methemoglobin), $HbO_2SAT$ (fraction of oxygen saturation), $O_2ct$ ($O_2$ content) and $O_2cap$ (oxygen capacity). The relationships between these parameters and directly calculated concentration values appear from the equations below:

$$tHb = cRHb + cHbO_2 + cHbCO + cMetHb$$

$$RHb = \frac{cRHb}{tHb}$$

$$HbCO = \frac{cHbCO}{tHb}$$

$$HbO_2 = \frac{cHbO_2}{tHb}$$

$$MetHb = \frac{cMetHb}{tHb}$$

$$HbO_2SAT = \frac{cHbO_2}{cRHb + cHbO_2}$$

$$O_2ct = HbO_2 \cdot tHb$$

$$O_2cap = (HbO_2 + RHb) \cdot tHb$$

wherein cRHb is the measured concentration of deoxyhemoglobin, $cHbO_2$ the measured concentration of oxyhemoglobin, cHbCO the measured concentration of carboxyhemoglobin, cMetHb the measured concentration of methemoglobin and tHb the sum of the concentrations of these derivatives.

As will be understood, the normal calculation of the derived parameters will involve first calculating the direct parameters and then treating them in accordance with the relationships above, but it is, of course, also within the scope of the invention to perform the mathematical calculation in any manner which would not first result in the direct parameters.

$$\text{Optionally, } SHb = \frac{cSHb}{tHb}$$

(fraction of sulfhemoglobin) may also be determined and is in fact determined and used in the presently preferred embodiment.

The wavelengths of the light used in the method according to the invention are normally chosen from the visible or near infrared range where the hemoglobin derivatives have a relatively high absorption such as appears from FIG. 7 which is discussed in the following. It is, however, within the scope of the invention to use light of wavelengths from any other spectral range in which the hemoglobin derivatives show sufficient absorption for the spectrophotometric system in question.

In the practical embodiment of the present invention, suitable wavelengths for measurement have been found to be 535, 560, 577, 622 and 636 nm as wavelengths at which the hemoglobin derivatives show a satisfactory absorption, but it will be evident to one skilled in the art that also other individual wavelengths in the range in question could be used for the measurement. A further wavelength at which a measurement is made in accordance with the principles of the present invention is suitably a wavelength at which the ratio between light scattering or apparent absorption exerted by turbidity and absorption exerted by hemoglobin derivatives is relatively high. As an example, a wavelength of above 650 nm, for example a wavelength of about 670 nm, has been found suitable.

The calculation of the concentration of each of the hemoglobin derivatives or the parameters derived from the concentration of individual hemoglobin derivatives may be performed using any suitable calculation means, such as in a separate calculator, an analog computer connected to the spectrophotometric equipment or, preferably, in a digital microprocessor after an analog/-digital conversion of the spectrophotometrically measured absorbances.

In the present context, the term "the modification of the incident light" comprises the absorbance, the transmittance or any suitable corresponding property expressing the influence of the blood on the light transmitted to the blood. Also, the term "light absorption characteristic" is to be understood in the broad sense as indicating a property inherent to the hemoglobin derivative at the wavelength in question. Similarly, "an absorption characteristic of turbidity" designates an apparent absorption inherently exerted by turbidity due to light scattering, such as is explained below.

The above-mentioned predetermined coefficient representing the light absorption characteristic of each of the hemoglobin derivatives at each of the wavelengths may be the absorptivity or the extinction coefficient or, alternatively, any other coefficient representing a unique hemoglobin derivative-dependent absorption behaviour at the particular wavelength.

The predetermined coefficient representing an absorption characteristic of turbidity at each of the wavelengths may, analogously, be a coefficient measured in the same manner as one would measure the extinction coefficient, in other words a coefficient analogously useful in the calculation of the concentration of the single components as if turbidity would behave in accordance with the Lambert-Beer's law. The coefficient representing an absorption characteristic of turbidity at each of the wavelengths may be determined empirically, for example by spectrophotometrical measurements on specially prepared plasma samples comprising standard "concentrations" of components incurring turbidity such as it is illustrated, e.g., in Example 2. In this context, it should be mentioned that the "absorption characteristics of turbidity" are values dependent on the optical configuration of the instrument type in question. This is because the turbidity does not give rise to an absorption proper, but rather to a reduction in transmitted light due to scattering. The absorption characteristics given below have been determined on a prototype instrument of the type described in the detailed part of the specification and shown in the drawings.

In accordance with what has been explained above and presuming (such as has been found reasonable) that blood containing turbidity can be treated in a similar manner as blood without turbidity, the relationship between the absorbances and the concentrations of each of the hemoglobin derivatives and "the concentration of turbidity" will be as follows:

$$A^{\lambda 1} = l(\epsilon_1^{\lambda 1''} \cdot C_1 + \epsilon_2^{\lambda 1} \cdot C_2 \ldots \epsilon_6^{\lambda 1} \cdot C_6)$$
$$A^{\lambda 2} = l(\epsilon_1^{\lambda 2} \cdot C_1 + \epsilon_2^{\lambda 2} \cdot C_2 \ldots \epsilon_6^{\lambda 2} \cdot C_6)$$

(Equation System I)

$$A^{\lambda 6} = l(\epsilon_1^{\lambda 6} \cdot C_1 + \epsilon_2^{\lambda 6} \cdot C_2 \ldots \epsilon_6^{\lambda 6} \cdot C_6)$$

wherein $A^{\lambda 1}$ represents the absorbance of the sample at a first wavelength, $A^{\lambda 2}$ represents the absorbance of the sample at a second wavelength, l represents the light path length, $\epsilon_1^{\lambda 1}$ represents the extinction coefficient characteristic of hemoglobin derivative 1 at the wavelength $\lambda 1$, $C_1$ is the concentration of hemoglobin derivative 1, etc., and one of the indices, for example 6, indicates the "component" turbidity.

Actual measured absorbance values on pure hemoglobin derivatives each at a concentration of 1 mmol/l are given below:

| Derivative | λ | Absorbance (ε · l) |
|---|---|---|
| RHb | 535.0 | .8510 |
| | 560.0 | 1.2080 |
| | 577.0 | .8945 |
| | 622.0 | .1203 |
| | 636.0 | .0956 |
| | 670.0 | .0679 |
| HbO₂ | 535.0 | 1.1427 |
| | 560.0 | .7867 |
| | 577.0 | 1.3424 |
| | 622.0 | .0234 |
| | 636.0 | .0156 |
| | 670.0 | .0097 |
| HbCO | 535.0 | 1.2562 |
| | 560.0 | 1.1220 |
| | 577.0 | .9498 |
| | 622.0 | .0303 |
| | 636.0 | .0170 |
| | 670.0 | .0053 |
| SHb | 535.0 | .7549 |
| | 560.0 | .7890 |
| | 570.0 | .8138 |
| | 622.0 | 2.3780 |
| | 636.0 | .9596 |
| | 670.0 | .1457 |
| MetHb | 535.0 | .6573 |
| | 560.0 | .4302 |
| | 577.0 | .4187 |
| | 622.0 | .3393 |
| | 636.0 | .3259 |
| | 670.0 | .0395 |

RHb designates deoxyhemoglobin, HbO₂ designates oxyhemoglobin, HbCO designates carboxyhemoglobin, SHb designates sulfhemoglobin, MetHb designates methemoglobin.

Actual measured absorbance values on a turbid solution as represented by a solution of 90% plasma and 10% Intralipid ® (200 mg/ml of infusion liquid available from Kabi Vitrum A/S, Copenhagen (containing inter alia soy lecithin and glycerol) are:

| | | |
|---|---|---|
| Turb. | 535.0 | .4050 |
| | 560.0 | .3650 |
| | 577.0 | .3420 |
| | 622.0 | .2880 |
| | 636.0 | .2730 |
| | 670.0 | .2420 |

The actual light path length was approximately 0.0089 cm.

When Equation System I is solved with respect to the concentrations, the following system results:

$$C_1 = K_{1.1} \cdot A^{\lambda 1} + K_{1.2} \cdot A^{\lambda 2} \ldots K_{1.6} \cdot A^{\lambda 6}$$
$$C_2 = K_{2.1} \cdot A^{\lambda 1} + K_{2.2} \cdot A^{\lambda 2} \ldots K_{2.6} \cdot A^{\lambda 6}$$

(Equation System II)

$$C_6 = K_{6.1} \cdot A^{\lambda 1} + K_{6.2} \cdot A^{\lambda 2} \ldots K_{6.6} \cdot A^{\lambda 6}$$

When using the specific absorbances of Equation System I to determine the coefficients of Equation System II, the following specific equation system results:

$$\begin{aligned}
cRHb = & -22.292 \times A^{535.0} \\
& +17.612 \times A^{560.0} \\
& +8.675 \times A^{577.0} \\
& -10.019 \times A^{622.0} \\
& +22.862 \times A^{636.0} \\
& -15.384 \times A^{670.0} \\
cHbO_2 = & -4.550 \times A^{535.0} \\
& -8.891 \times A^{560.0} \\
& +16.561 \times A^{577.0} \\
& -1.895 \times A^{622.0} \\
& +1.883 \times A^{636.0} \\
& -2.247 \times A^{670.0} \\
cHbCO = & +25.128 \times A^{535.0} \\
& -2.101 \times A^{560.0} \\
& -20.073 \times A^{577.0} \\
& +14.333 \times A^{622.0} \\
& -39.033 \times A^{636.0} \\
& +16.462 \times A^{670.0} \\
cSHb = & +.114 \times A^{535.0} \\
& -.188 \times A^{560.0} \\
& -.026 \times A^{577.0} \\
& +7.278 \times A^{622.0} \\
& -7.519 \times A^{636.0} \\
& -.049 \times A^{670.0} \\
cMetH6 = & +.275 \times A^{535.0} \\
& -.429 \times A^{560.0} \\
& -.000 \times A^{577.0} \\
& -20.424 \times A^{622.0} \\
& +56.752 \times A^{636.0} \\
& -39.527 \times A^{670.0} \\
cTurb = & +5.773 \times A^{535.0} \\
& -4.356 \times A^{560.0} \\
& -2.642 \times A^{577.0} \\
& +1.525 \times A^{622.0} \\
& -10.371 \times A^{636.0} \\
& -51.850 \times A^{670.0}
\end{aligned}$$

According to the present invention the number of wavelengths at which measurement of the absorbance of the sample is performed is normally at least equal to the number of hemoglobin derivatives to be determined plus one.

While measurement at a number of wavelengths corresponding to the number of hemoglobin derivatives to be determined plus one will permit the constructing and solving of the above equation system, it is within the scope of the invention to measure the light modification of the blood at further wavelengths. This may be done, e.g., to obtain further data which can be used to check the correctness of the measurements by inserting the calculated values in a further equation, and/or to perform compensation for any further components in the blood sample which shows spectral absorption at one or several other wavelengths at which measurement is made. Such further components, typical of which are diagnostic dyestuffs such as Evan's Blue, Methylene Blue or Cardio Green and/or plasma pigments such as bilirubin or carotene, may suitably be compensated for by utilizing, in the calculation of the concentration of the hemoglobin derivatives, predetermined data representing an absorption characteristic of the component in question at each of the wavelengths at which measurement is made, and by utilizing data obtained by measurement in a further wavelength, normally a wavelength at which the ratio between absorption exerted by the component and absorption exerted by the hemoglobin derivatives is relatively high.

It is also within the scope of the invention to perform an even finer compensation for turbidity-induced errors by treating the tubidity as two or more individual components, e.g., three individual components: One component being turbidity arising due to the presence of relatively large particles such as erythrocytes, another component being turbidity arising due to the presence of lipid globules, and a third component being turbidity arising as a result of small residues such as cell debris, etc., in particular small residues resulting from an ultrasonic hemolyzation treatment. In accordance with the invention, this is done by measuring at a further wavelength for each additional turbidity component to be determined and performing the calculations based on coefficients including the individual turbidity components, these coefficients being suitably determined empirically in the same manner as mentioned above.

As appears from the above systems of equations, the "concentration" of turbidity can, if desired, be calculated on the basis of the data available. This calculation may suitably be utilized for checking that the turbidity value is below a predetermined level of acceptability. For example, it may be desirable that a warning is given to the operator if the turbidity value becomes so large that this, in spite of the compensation according to the invention, might be presumed to result in a significant influence on the calculated concentrations of the hemoglobin derivatives.

The method of the invention may be performed in vitro in an analytical apparatus on a sample of hemolyzed whole blood. Conceivably, the method may also be performed in connection with in vivo measurements on the living body as described, e.g., in the specification of U.S. Pat. No. 4,167,331, the contents of which is incorporated herein by reference.

Japanese Published application Kokai No. 54-084781 relates to a method for determinig the concentration of a substance (for example uric acid) in serum samples wherein the absorbance of the sample is determined by using at least four wavelengths, including a wavelength near the absorption centre of the substance to be examined. A number of equations utilizing predetermined standard spectra of the substances to be examined and of turbidity, hemoglobin and bilirubin are processed to determine the concentration of the substance examined, turbidity, degree of hemolysis and degree of jaundice, thereby obtaining a precise determination of the substance such as uric acid in the serum sample without disturbance from turbidity, hemoglobin and bilirubin. The patent specification does not indicate that it would be possible to obtain reliable and useful measurements of the concentration of hemoglobin derivatives and particularly the derived parameters thereof, especially the oxygen saturation fraction, in whole blood containing turbidity.

U.S. Pat. No. 4,357,105 relates to the spectrophotometric determination of the total content of hemoglobin in a hemolyzed blood sample by means of analog technique. The turbidity of the sample is determined by a measurement in the infrared range where hemoglobin does not adsorb. The patent states that the influence exerted by turbidity on the determination of the hemoglobin concentration can be corrected for by detracting the turbidity value thus found from the —too high — hemoglobin value found. As demonstrated in Example 1 below, such a procedure with correction for a fixed turbidity value would not result in any useful and reliable determination of the concentration of hemoglobin derivatives.

A commercial instrument, Corning 2500, determines hemoglobin derivatives basically in a manner closely corresponding to the instrument described in U.S. Pat. No. 3,927,614. For the determination of the concentration of hemoglobin derivatives, the instrument arrives at an indication of the presence of interfering substances (to which turbidity may pertain). However, the instrument does apparently not compensate for the error caused by turbidity such as is the gist of the present invention.

U.S. Pat. No. 4,167,331 relates to a noninvasive apparatus for the spectrophotometric determination of the oxygen saturation fraction-a so-called oximeter. An embodiment is described wherein the presence of an absorber apart from oxyhemoglobin and deoxyhemoglobin, e.g. a dye or carboxyhemoglobin, is dealt with by the addition of a third wavelength. Compensation for the presence of light scattering components such as turbidity are by no means contemplated.

The invention also relates to an apparatus for spectrophotometrically determining the concentration of a number of hemoglobin derivatives comprising at least deoxyhemoglobin and oxyhemoglobin or parameters derived from the concentration of individual hemoglobin derivatives in whole blood, in particular the oxygen saturation fraction, said apparatus comprising light source means for transmitting light to the blood under test, light detector means for receiving light modified by the blood, and measuring means for determining the light modification at a number of individual wavelengths and for determining the concentrations or the derived parameters on the basis of the light modification measured at the individual wavelengths and on the basis of predetermined coefficients representing the light absorption characteristics of each of the hemoglobin derivatives at each of the individual wavelengths, any error in the determinations due to turbidity being substantially compensated for by utilizing predetermined coefficients representing an absorption characteristic of turbidity at each of the individual wavelengths.

The light source means for emitting light to the blood may be a single light source which may comprise an assembly of monochromatic light sources adapted to sequentially transmit light of each of said wavelengths to the blood, or the means may comprise a single light source cooperating with a set of optical filters each of which allows for the transmission of light of a single wavelength, the filters being sequentially positionable in the front of the light source so that light of each of the single wavelengths is sequentially transmitted to the blood. However, in a presently preferred embodiment, the light source means is a conventional light source generating a broad band, the division into individual wavelengths being performed after modification of the light caused by the blood by means of, e.g., an optical grating device as will be explained in greater detail below.

The measuring means of the apparatus may be implemented in hardware by employing measuring amplifiers and weighting networks constituting a matrix weighting circuit, or it may, in a further embodiment, comprise a computer means which suitably includes storage means for storing data representing the predetermined coefficients of a number of hemoglobin derivatives at each of the individual wavelengths and for storing data representing the coefficients representing the absorption characteristic of turbidity at each of the individual wavelengths and further a calculating means for calculating the oxygen saturation, the hemoglobin derivatives concentrations or the derived parameters of the hemoglobin derivatives on the basis of the light modification measured at the individual wavelengths and the said data.

In a preferred embodiment, the apparatus according to the invention comprises sample inlet means, hemolyzation means, a conduit for conducting the sample from the sample inlet means through the apparatus, the conduit having transparent wall parts defining a light transmission path through a blood sample positioned in the conduit, light source means for emitting light to the light transmission path and light detector means for receiving light transmitted through the blood sample.

The hemolyzation of the blood sample may either have been performed in an auxiliary hemolyzer or within hemolyzing means included in the apparatus.

Hemolyzation may be performed by various means, e.g. a chemical hemolyzing agent, sound or ultrasound. In a preferred embodiment, the hemolyzing means is included in the apparatus and comprises an ultra-sonic sound generator means for radiating ultra-sonic sound energy to the sample in the sample conduit of the apparatus.

Another embodiment of the apparatus according to the invention comprises means for positioning the apparatus against living tissue so as to provide a light transmission path from the light source means via the living tissue to the light detector means.

The invention will now be further described with reference to the drawings, wherein.

Figure 1:
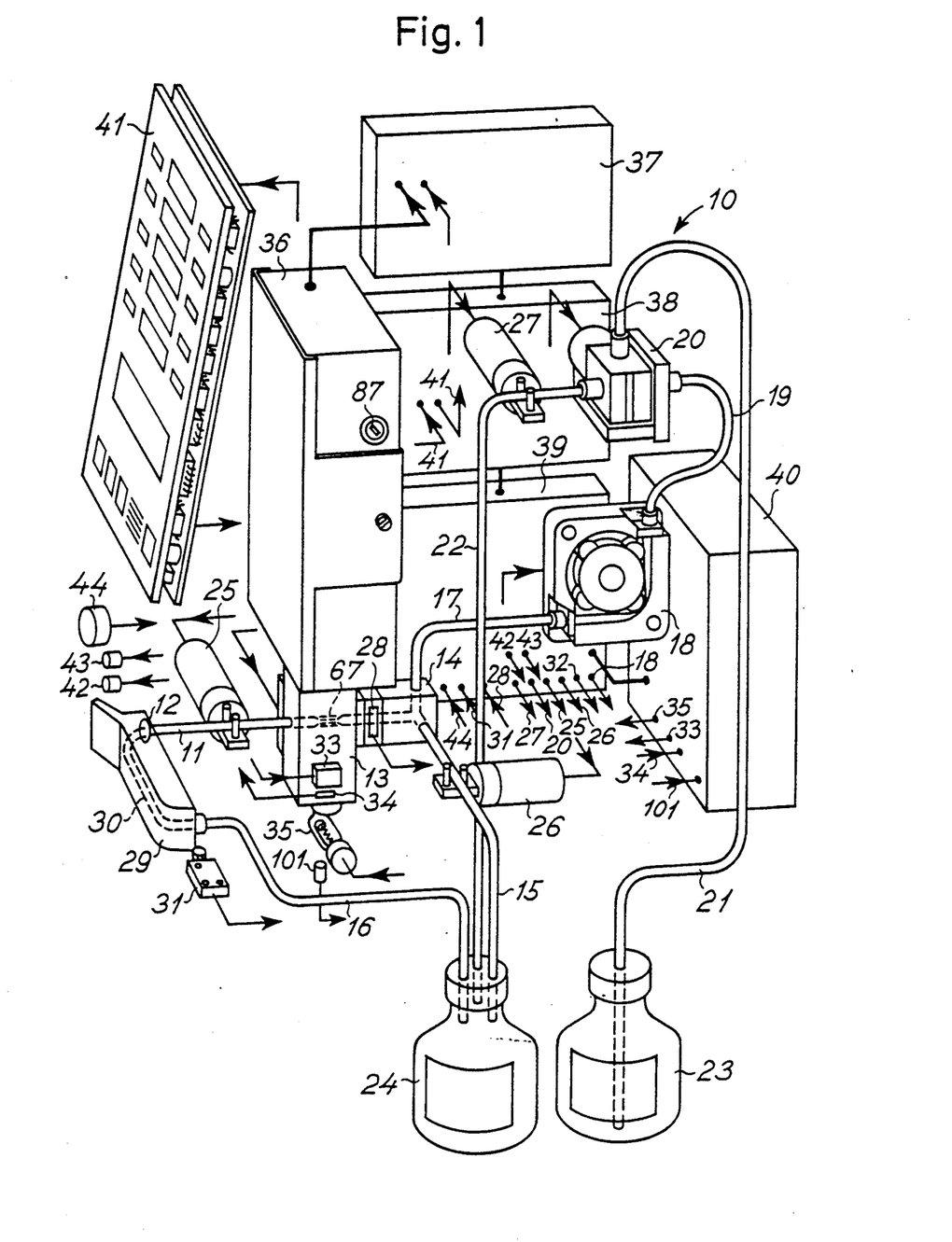
FIG. 1 is a perspective and overall schematic view of a presently preferred embodiment of an apparatus according to the invention.

In FIG. 1, a presently preferred embodiment of an apparatus according to the invention for determining inter alia oxygen saturation or oxygen content of a blood sample by determining a total of five hemoglobin derivatives in accordance with the method according to the invention, is shown designated by the reference numeral 10 in its entirety. The apparatus 10 includes a fluid tube or conduit system comprising an inlet tube 11 extending from an aperture 12 at an outer side surface of the housing of the apparatus to a hemolyzing and measuring block 13 and further to a liquid detector and liquid conduit divider block 14, in which a liquid detector 28 is arranged, and therethrough, a first waste tube 15, a second waste tube 16, a tube section 17 extending from the liquid detector and liquid conduit divider block 14 to a pump 18, a further tube section 19 extending from the pump 18 to a three-way valve 20, a rinsing liquid inlet tube 21 and further an air suction tube 22. The rinsing liquid inlet tube 21 is immersed in a rinsing liquid contained in a rinsing liquid container 23 and extends from the rinsing liquid container 23 to the three-way valve 20. The first and second waste tubes 15 and 16 and the air suction tube 22 extends into a waste container 24, preferably only into the upper part thereof as indicated by dotted lines in FIG. 1.

The liquid transfer through the inlet tube 11 is controlled by an inlet tube valve 25. Similarly, the liquid transfer through the second waste tube 15 and through the air suction tube 22 is controlled by a first waste tube valve 26 and an air suction tube valve 27, respectively. A manually operable inlet flap 29 includes a through-going conduit 30 which provides liquid communication between the inlet tube 11 and the second waste tube 16 in the "closed" position of the inlet flap 29 shown in FIG. 1. In the alternative or "open" position of the inlet flap 29, the liquid communication between the inlet tube 11 and the second waste tube 16 is interrupted. The positioning of the inlet flap 29 is detected by a positioning detector or micro switch 31.

Within the above-mentioned hemolyzing and measuring block 13 and thus not shown on the drawing, a hemolyzing ultra-sonic generator, in the following designated 32, is contained. The block 13 is thermostatically heated to a predetermined temperature, preferably a temperature of 37° C., and includes a heater 33 constituted by a power transistor and a temperature sensor 34 constituted by an NTC-resistor. Below the lower side surface of the hemolyzing and measuring block 13, a light emitting device 35 constituted by a photo lamp is arranged. The intensity of the light emitted from the light emitting device 35 is detected by a light detector 101 constituted by a photodiode. The light detector is connected to a control circuit which supplies power to the light emitting device 35 and serves the purpose of maintaining a constant intensity of light radiated from the light emitting device 35. Part of the light emitted from the light emitting device or photo lamp 35 is transmitted through the blood sample contained in a cuvette 67 which constitutes part of the conduit extending through the hemolyzing and measuring block 13 and is optically processed in a monochromator assembly 36 to be described in greater detail below with reference to FIGS. 3, 4 and 5. Measuring signals generated in the monochromator assembly 36 are input to a signal processor 37 which further communicates with a central microcomputer 38 in which the measuring signals generated in the monochromator assembly 36 and processed in the signal processor 37 are further processed in accordance with the measuring method of the present invention and which controls the functions and operations of the apparatus. The central microcomputer 38 also communicates with a control interface 39 through which the central microcomputer 38 controls the operations of the pump 18, the valves 20, 25, 26 and 27 and the ultra-sonic generator 32 contained within the hemolyzing and measuring block 13 and through which the central microcomputer 38 also receives control signals from the liquid detector 28 and the micro switch 31. The apparatus 10 further comprises a power supply section 40 which supplies power to the photo lamp 35 and includes the above constant light intensity control circuit, a display 41, which is shown in greater detail in FIG. 2, two indicator lamps 42 and 43 and a push button switch 44.

Before turning to a detailed description of the operation of the embodiment of the invention shown in FIG. 1, it is to be mentioned that the small dimensions of the inlet tube 10, i.e. the small cross-sectional area and the small length thereof, renders it possible to determine oxygen saturation or oxygen content of a blood sample being as small as 35 $\mu l$.

It is assumed that the apparatus is initially rinsed and further calibrated, i.e. that no blood sample or no rinsing liquid is present in the tubes of the apparatus and that the apparatus has been calibrated by employing the rinsing liquid as will be described below. The apparatus is ready to receive a blood sample which is indicated to an operator by the lamp 42 which is a "ready" lamp. In the "ready"-state, the valves 25, 26 and 27 are open, the three-way valve 20 closed, and the pump 18 is not in operation. The operator opens the inlet flap 29 in order to expose the aperture of the inlet tube 11 for the introduction of a blood sample into the inlet tube 11. By the opening of the inlet flap 29, the liquid communication through the conduit 30 between the inlet tube 11 and the second waste tube 16 is interrupted and the opening of the inlet flap 29 further activates the micro switch 31 thus generating a signal which is supplied to the central microcomputer 38 informing the central microcomputer 38 that the inlet flap 29 has been opened.

The blood sample may be introduced by injection, i.e. the operator may inject the blood sample into the inlet tube 21 by means of a syringe. When the blood sample reaches the liquid detector 28 of the liquid detector and liquid conduit divider block 14, the liquid detector 28 supplies a liquid detection signal to the central computer 38 which turns off the "ready" lamp 42 and turns on the "busy" lamp 43 informing the operator that the conduit of the hemolyzing and measuring block 13 of the apparatus 10 is filled with the liquid sample. Any excess liquid injected into the inlet tube 11 by the operator flows through the first waste tube 15 and into the waste container 24.

The blood sample may alternatively be introduced into the inlet tube 11 by aspiration through an external tube, not shown in FIG. 1, which is mounted on a free end of the inlet tube 11 and extends into a blood sample container, not shown in FIG. 1 either. The operator pushes the push button switch 44 by which an aspiration signal is supplied to the control interface 39. The valve 26 is closed and the pump 18 is activated for introducing the blood sample into the inlet tube 11 by suction. When the blood sample reaches the liquid detector 28 of the liquid detector and liquid conduit divider block 14, the liquid detector supplies a liquid detection signal to the central microcomputer 38, as explained above, whereupon the central microcomputer 38 switches off the pump 18 and further turns off the "ready" lamp 42 and turns on the "busy" lamp 43.

Now, the operator removes the syringe or alternatively the abovementioned external tube from the free end of the inlet tube 11 and closes the inlet flap 29. The liquid communication between the inlet tube 11 and the second waste tube 16 through the through-going conduit 30 of the inlet flap 29 is re-established and the positioning of the inlet flap 29 in the position shown in FIG. 1, i.e. in the closed position, is detected by the micro switch 31 which supplies a signal to the central microcomputer 38 representing the positioning of the inlet flap in the position shown in FIG. 1.

The apparatus is now ready to proceed to the next stage of the operational routine of the apparatus. In order to avoid formation of gas bubbles within the cuvette 67 of the hemolyzing and measuring block 13 and improve the effectiveness of the hemolyzation procedure, the blood sample present in apparatus is pressurized. The central microcomputer 38 closes the valve 25 and further the valve 26 provided the valve 26 has not previously been closed, and further activates the pump 18 for pressurizing the tube section 17 and further the blood sample present in the conduit of the blocks 13 and 14. After the central microcomputer 38 has turned off the pump 18, the central microcomputer 38 activates the ultra-sonic generator 32 in order to hemolyze the blood sample present within the measuring cuvette 67 of the hemolyzing and measuring block 13.

The apparatus is ready to proceed to the next stage or the measuring stage of the operational routine. The control interface 39 addresses the power supply section 40 in order to make the power supply section 40 supply power to the light emitting device or photo lamp 35 for a period of time during which the hemoglobin derivatives are determined from the measuring signals which are supplied from the monochromator assembly 36 which are subsequently processed in the signal processor 37 and further processed in the central microcomputer 38 in accordance with the measuring method of the present invention, as will be described below in greater detail.

After the conclusion of the determination of the hemoglobin derivatives of the sample, the apparatus proceeds to a rinsing stage of the operational routine. In the rinsing stage, air and rinsing liquid are intermittently transferred through the tubes of the apparatus in a so to speak air-liquid droplets train. The air-liquid droplets train is generated by activation of the pump 18 for suction through the tube section 19 and by intermittently opening and closing the valve 27 and the three-way valve 20 for suction air and rinsing liquid, respectively, through the air suction tube 22 and through the rinsing liquid inlet tube 21, respectively. The air-liquid droplets train is supplied to the liquid detector and liquid conduit divider block 14 through the tube section 17 and further transferred through the first waste tube 15 or through the inlet tube 11, through the through-going conduit 30 and through the second waste tube 16 by intermittently opening and closing the valves 25 and 26. After the rinsing of the tubes by means of the air-liquid droplets train, the central microcomputer 38 closes the valve 27 and opens the three-way valve 20 for transferring a continuous rinsing liquid supply through the tubes of the apparatus in order to remove any droplets present in the tubes or in the conduits of the apparatus. Finally, a continuous air string is drawn through the tubes of the apparatus in order to remove reminiscences of rinsing liquid.

Figure 2:
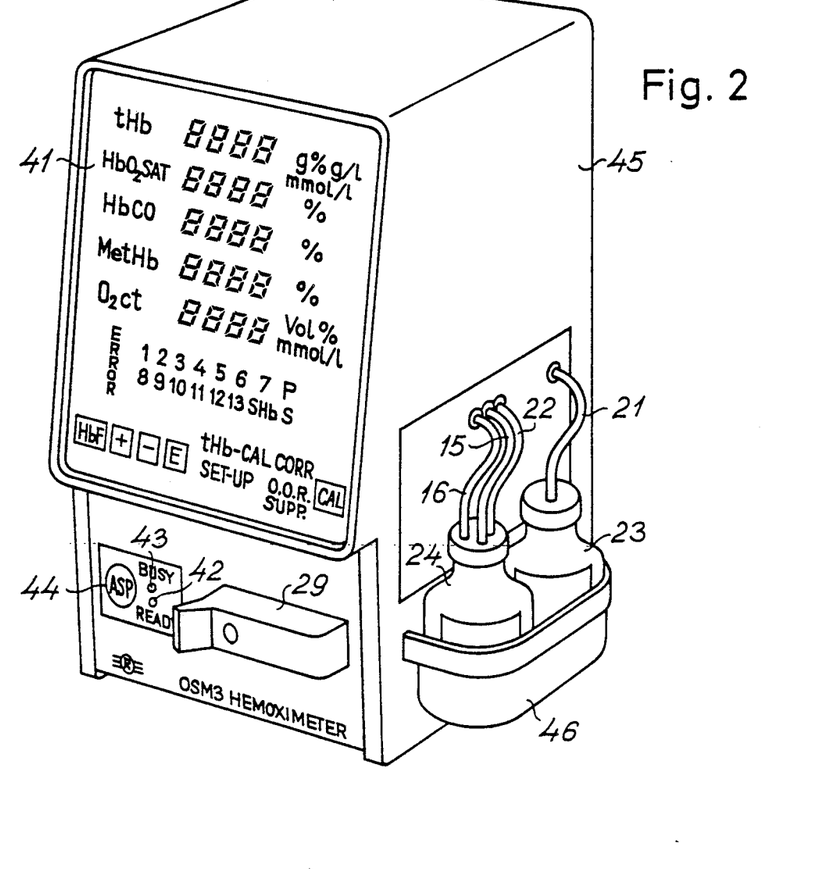
FIG. 2 is a schematic view of the housing of the presently preferred embodiment of the apparatus according to the invention.

In FIG. 2, the above described presently preferred embodiment of the apparatus according to the invention is shown. Apart from the above described components, the apparatus comprises a housing 45 on the right-hand side of which a receptacle 46 is arranged for receiving therein the rinsing liquid container 23 and the waste container 24. The front surface of the housing 45 is divided into an upper sloping part in which the display 41 is arranged recessed in relation to the outer walls of the housing and a lower part in which the inlet flap 29, the indicator lamps 42 and 43 and the aspiration push button 44 are mounted.

Figure 3:
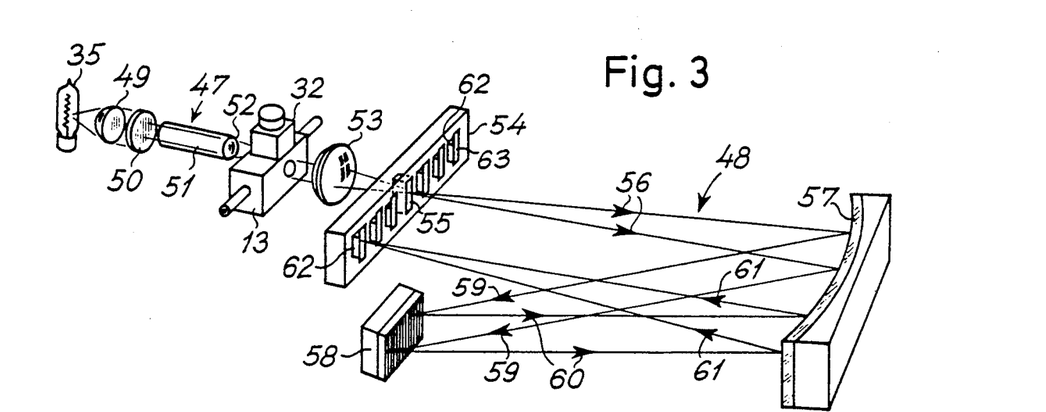
FIG. 3 is a schematic and perspective view of the optical section of the presently preferred embodiment of the apparatus according to the invention.

In FIG. 3, the optical system of the above monochromator assembly 36 is shown. The optical system comprises an input part 47 serving the purpose of transmitting light from the light emitting device or photo lamp 35 to the blood sample contained in the cuvette 67 of the hemolyzing and measuring block 13, and an output part 48 serving the purpose of guiding or transmitting light transmitted through the blood sample contained in the cuvette 67 of the block 13 to a plurality of light detectors. The input part 47 which is an integral assembly includes a plane convex lens 49, an infrared absorbing filter 50, and light guide 51 having a convex end portion 52. The output part 48 comprises a biconvex lens 53, an optical screening device 54 having an aperture aligned in relation to the light transmission path of the biconvex lens, the block 13 and the input part 47, and further a concave mirror 57 and an optical grating device 58. From the aperture 55 of the optical screening device 54 the light is transmitted to the concave mirror 57 as indicated by arrows 56 and further to the optical grating device 58 serving the purpose of separating the light transmitted to the grating device into monochromatic components. The light transmitted from the concave mirror 57 to the optical grating device 58 is indicated by arrows 59. Part of the light transmitted to the optical grating device 58 is re-transmitted to the concave mirror 57 as indicated by arrows 60 and further from the concave mirror 57 to the screening device 54.

The screening device 54 is a plane and hollow device in which a plurality of light detectors or photodiodes 62 are housed. In the presently preferred embodiment of the apparatus according to the invention shown in the drawings, a total of six photodiodes 62 are arranged in the optical screening device 54. The individual light detectors or photodiodes 62 are exposed to monochromatic or substantially monochromatic light separated in the grating device 58 and reflected from the concave mirror 57. The monochromatic or substantially monochromatic light is transmitted to the individual light detectors or photodiodes 62 through slits or apertures 63 of the front surface of the screening device 54 facing the concave mirror 57. Basically, the optical system of the apparatus according to the invention is a modification of the so-called Littrow-system. It is to be mentioned that the light re-transmitted from the optical grating device 58 to the concave mirror 57 is reflections of first order.

Figures 4, 5:
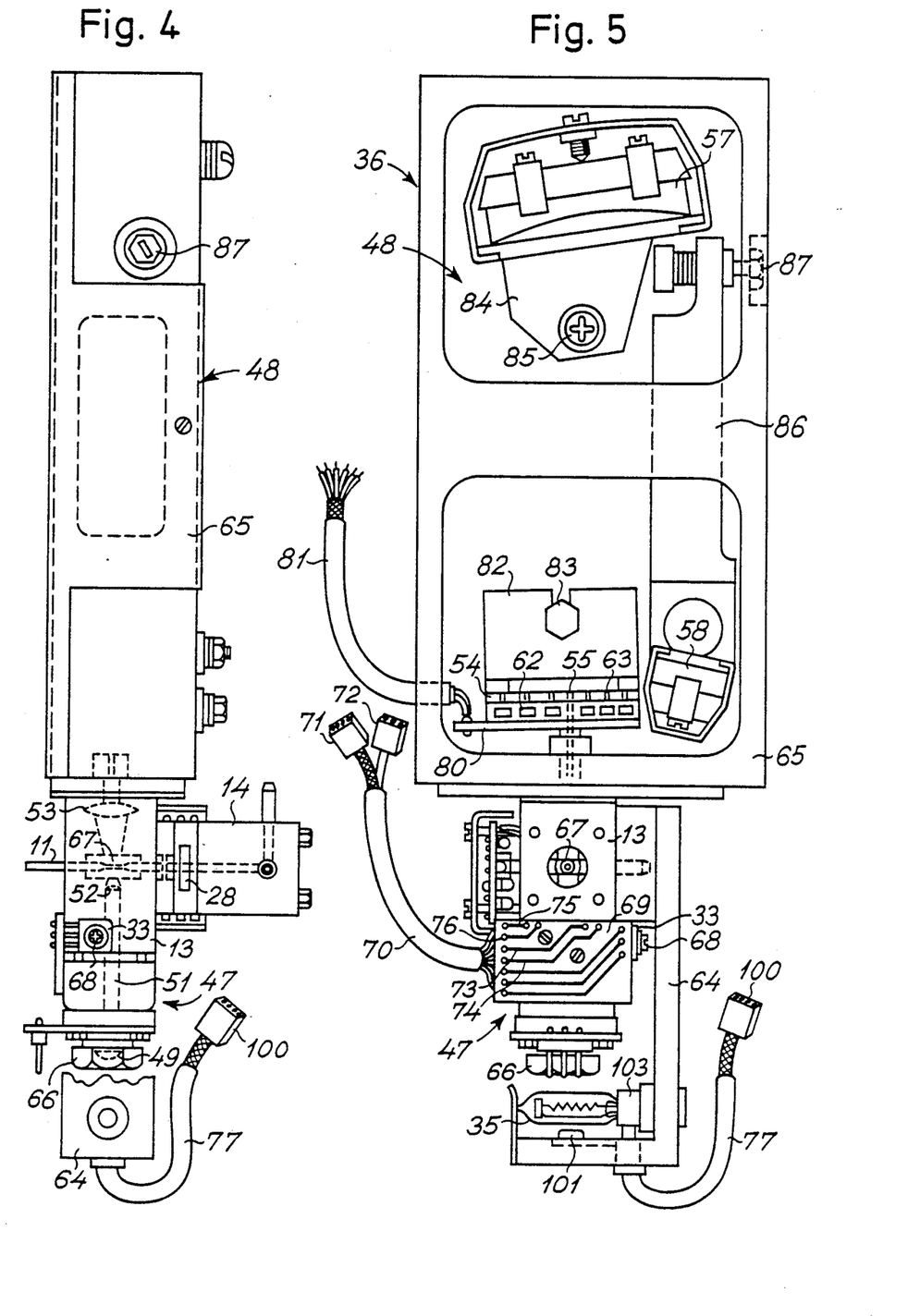
FIGS. 4 and 5 are detailed plane views of the optical section shown in FIG. 3.

In FIGS. 4 and 5, the monochromator assembly shown in FIG. 1 and described above with reference to FIG. 3 is shown in greater detail in plane orthogonal views. In the lower parts of FIGS. 4 and 5, the above described part 47 is shown and in the upper parts of FIGS. 4 and 5, the above output part 48 is shown. The light emitting device or photo lamp 35 is mounted in a lamp receptacle or socket 103, which is further mounted on a lamp supporting bracket 64. The lamp supporting bracket 64 is fastened to a housing 65 which includes the above output part 48 and on which the above hemolyzing and measuring block 13 is further mounted. As is evident from FIG. 4, the plane convex lens 49 is mounted in a lens holder 66 which is also shown in FIG. 5, and the components defining the light transmission path from the plane convex lens 49 are shown in dotted lines. The light emitted from the convex end portion 52 of the light guide 51 is radiated to the cuvette 67 also shown in FIG. 1 which defines part of the blood sample containing conduit of the block 13. As described above, the light transmitted through the conduit of the block 13, i.e. through the cuvette 67 and through the material, i.e. the blood sample included therein, is as indicated in dotted lines in FIG. 4 transmitted to the biconvex lens 53, which is also shown in dotted lines in FIG. 4.

The above described liquid detector 28 of the liquid detector and liquid divider block 14 as well as the block 14 are shown in FIG. 4. The above heater 33 serving the purpose of heating the block 13 to a predetermined temperature, preferably 37° C., is also shown in FIG. 4. The heater 33 which is constituted by a power transistor is mounted in heat-conductive contact with the block 13 by means of a fixation screw 68. The fixation screw 68 is also shown in FIG. 5, which further discloses the mounting of the power transistor 33 on a printed circuit board 69. As is evident from FIG. 5, a multi-core cable 70 is also mounted on the printed circuit board 69 for establishing connection between the circuit board 69 and further the components arranged thereon and the power supply section 40 through a multi-pin plug or socket 71 and for establishing connection between the ultrasonic generator 32 and the control interface 39 through a multi-pin plug or socket 72. On the printed circuit board 69, the temperature sensor 34 shown in FIG. 1 is also mounted and connected to the multi-core cable 70 through printed circuit tracks 73 and 74 of the printed circuit board 69. A further temperature sensor, not shown in FIG. 1, is also mounted on the printed circuit board 69 and connected to the multi-core cable 70 through printed circuit tracks 75 and 76.

As mentioned above, the power supply section 40 also supplies power to the lamp 35 and via a control interface 39 to the ultrasonic generator 32 of block 13 controlled by the central microcomputer 38. The power supplied from the power supply section 40 to the lamp 35 is transmitted through a second multi-core cable 77 which is provided with a multi-pin plug or socket 100 and which also transmits the light intensity signal generated by the photodiode 101 to the above-mentioned constant high intensity control circuit of the power supply section 40.

The ultra-sonic energy generated by the ultra-sonic generator 32 of block 13 is of a frequency of 40 kHz. The hemolyzation of blood by employing ultra-sonic sound energy is described in U.S. Pat. No. 3,972,614.

In the housing 65, the above described optical screening device 54 is mounted adjacent to the lower housing wall of the housing 65. The screening device 54 and the light sensors or photodiodes 62 mounted therein are arranged on a printed circuit board 80 to which a third multi-core cable 81 is connected. The third multi-core cable 81 serves the purpose of transmitting signals generated by the light detectors or photodiodes 62 to the signal processor 37 shown in FIG. 1. As is evident from FIG. 5, the printed circuit board 80 is mounted on a supporting device 82 which is bolted to the housing 65 by means of a screw 83 and defines an angle of 1.4° in the plane of FIG. 5 relative to a direction perpendicular to the light transmission path from the plane convex lens 49 through the aperture 55 of the screening device 54.

The concave mirror 57 is mounted on a supporting member 84 which is fixed relative to the housing 65 by means of a screw 85. The optical grating device 58 is mounted on a supporting rail or supporting member 86. The angular position of concave mirror 57 in relation to the optical grating device 58 is determined by a set screw 87 which extends through the outer wall of the housing 65 as is also evident from FIG. 1. By rotating the set screw 87, the optical grating device 58 is rotated.

Figure 6:
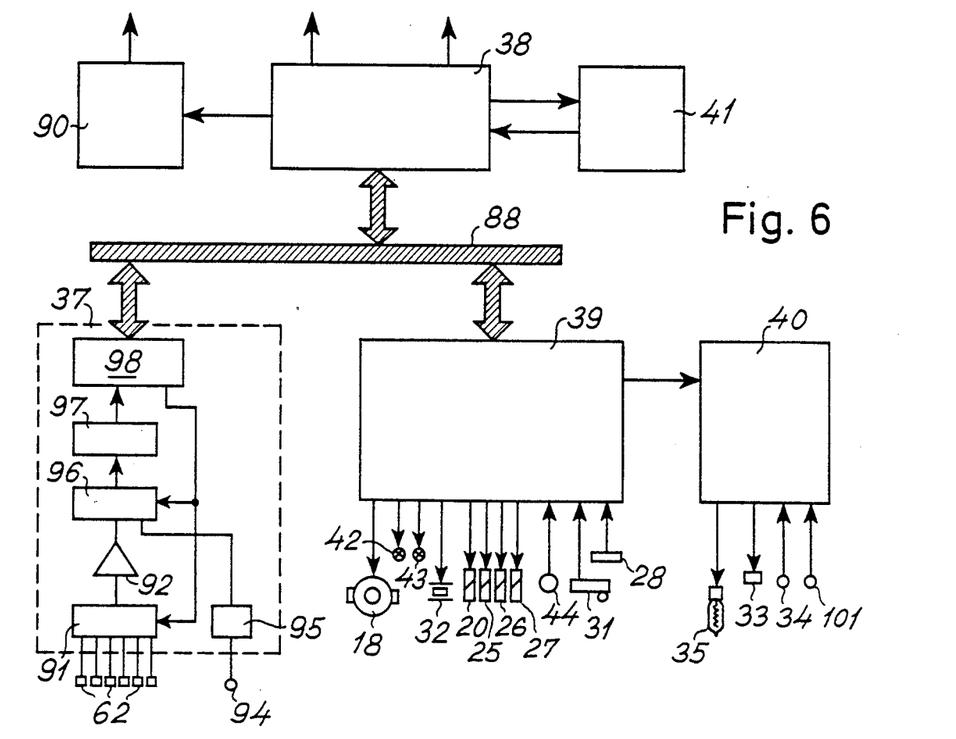
FIG. 6 is an overall block diagram of the electronic circuitry of the presently preferred embodiment of the apparatus according to the invention.

In FIG. 6, a block diagram of the electronic circuitry of the presently preferred embodiment of the apparatus according to the invention is shown. The above-mentioned signal processor 37 is shown in a dotted line block, the individual components or blocks of which will be described in greater detail below. The signal processor 37, the central microcomputer 38 and the control interface 39 communicate with one another through a bus 88. Through the control interface 39, the central microcomputer 38 further communicates with or controls the power supply section 40 which supplies power to the light emitting device or photo lamp 35 and further to the heater 33 shown in FIG. 1 and the temperature sensor 34, also shown in FIG. 1. Together with the control interface 39, the above described pump 18, the lamps 42 and 43, the ultra-sonic generator 32, the valves 20, 25, 26, and 27, the push button 44, the micro-switch 31, and the liquid detector 28 are shown in FIG. 6.

As described above, the central microcomputer 38 communicates with the display 41 and further with an interface block 90 for transmission of the measuring results generated there and displayed on the display 41 to external equipment, e.g. a printer or data logging equipment, an external computer or the like.

As described above with reference to FIG. 5, the signal processor 37 is connected to the light detectors or photodiodes 62 of the optical screening device 54 through the multi-core cable 81. In order to reduce the number of measuring amplifiers of the signal processor, the photodiodes 62 are connected to the inputs of a first time division multiplexer block 91. The output of the time division multiplexer block 91 is connected to the input of a logarithmic amplifier 92. The light detectors or photodiodes 62 are constituted by photodiodes sensitive to light of a wavelength of approximately 400 nm–1000 nm. The photodiodes of the above described presently preferred embodiment of the apparatus according to the invention generate photodiode currents of the order of 1–400 nA. The logarithmic amplifier converts the photodiode current to 4 V/dec; 0 V = 1 $\mu$A. The temperature of the hemolyzing and measuring block 13 is further detected by means of a temperature sensor 94 which is connected to the input of a temperature signal amplifier 95. The outputs of the logarithmic amplifier 92 and of the temperature signal amplifier 95 are connected to a second time division multiplexer block 96. From the output of the second time division multiplexer block, normalized measuring signals representing the temperature detected by means of the temperature sensor 94 and the light intensities detected by the photodiodes 62 are input to an analog/digital converter 97. The output of the analog/digital converter 97 is connected to an interface input/output block 98 the output of which is connected to the bus 88.

The routine calibration of the instrument is suitably performed by introducing rinse liquid into the cuvette 67 instead of the blood sample, measuring the intensity of the light transmitted through the rinse liquid at the measuring wavelengths to obtain calibration values and subtracting the calibration values from the values measured on the blood samples at each wavelength.

Figure 7:
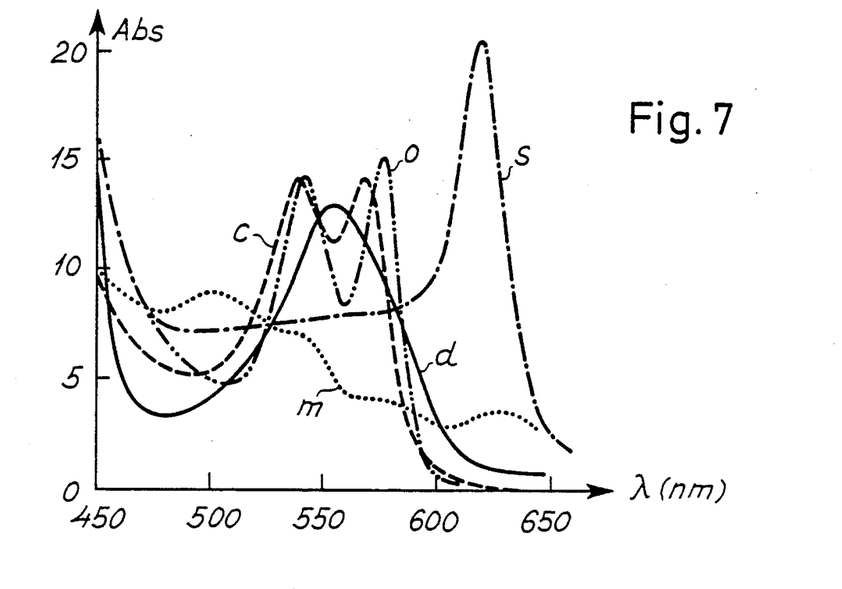
FIG. 7 is a diagram illustrating absorption spectra of deoxy- or reduced hemoglobin, oxyhemoglobin, carboxyhemoglobin, methemoglobin, and sulfhemoglobin within the range of 450–650 nm.

FIG. 7 illustrates absorption spectra of the hemoglobin derivatives deoxyhemoglobin (d), oxyhemoglobin (o), carboxyhemoglobin (c), methemoglobin (m) and sulfhemoglobin (f) within the range of 450–660 nm. The molar absorptivity or extinction coefficient for each derivative is plotted against wavelength.

EXAMPLE 1

Using an instrument as described in connection with the drawings, determination of total hemoglobin, oxyhemoglobin, carboxyhemoglobin and methemoglobin was performed on blood samples as withdrawn and blood samples mixed with Intralipid ®.

The samples were prepared in the following manner:

Three blood samples (from a voluntary donor, healthy, non-smoker) were equilibrated for 0.5 hour with a gas mixture containing 4% of $CO_2$ and 96% of $O_2$ in a film tonometer. This treatment is known to result in substantially all hemoglobin of the samples being present as oxyhemoglobin.

One sample (in the following termed sample A, $HbO_2$) was used for the measurements without further treatment. Another sample (sample B, $HbO_2$) was admixed with Intralipid ® in a ratio of 95% by volume of the sample to 5% by volume of Intralipid ®. Another sample (sample C, $HbO_2$) was mixed with Intralipid ® in a ratio of 90% by volume of the sample and 10% of Intralipid ®. The above described equilibration of the blood for the samples A, B, and C aims at all the hemoglobin of the sample being present as $HbO_2$, in other words corresponding to:

| | |
|---|---|
| $HbO_2SAT$ | 100% |
| HbCO | 0% |
| MetHb | 0% |

Two blood samples (D and E) (obtained from blood of non-smokers) were centrifuged, and 3 ml of concentrate derived from 5 ml of the sample were mixed with 2 ml of a reduction liquid of the composition

| | |
|---|---|
| 44 mg | Tris |
| 62 mg | $Na_2S_2O_4$ |
| 5 ml | ionized water | in a glass syringe. In this manner, substantially the total content of hemoglobin in the samples is converted to deoxyhemoglobin. The samples were hemolyzed as described above.

A portion of sample D was mixed with Intralipid ® in a ratio of 95% by volume of the sample to 5% by volume of Intralipid ®, and a portion of sample E was mixed with Intralipid ® in a ratio of 90% by volume of sample E to 10% by volume of Intralipid ®. The above-described reduction of the samples D and E aims at the following values:

| | |
|---|---|
| $HbO_2SAT$ | 0% |
| HbCO | 0% |
| MetHb | 0% |

The spectral absorptions of the samples at the wavelengths 535, 560, 577, 622, 636 and 670 nm were measured in a prototype of the instrument described in connection with the figures. Based on the absorptions, calculations of the percent concentrations of oxyhemoglobin, carboxyhemoglobin and methemoglobin were performed in three different manners:

(1) Using a laboratory equation matrix with the values given in the section "DISCLOSURE OF INVENTION" above.
(2) Using a matrix comprising 5 measurements and 5 equations based on the following non-normalized coefficients:

| Derivative | λ | Coefficient |
|---|---|---|
| RHb | 535.0 | .8510 |
|  | 560.0 | 1.2080 |
|  | 577.0 | .8945 |
|  | 622.0 | .1203 |
|  | 636.0 | .0956 |
| $HbO_2$ | 535.0 | 1.1427 |
|  | 560.0 | .7867 |
|  | 577.0 | 1.3424 |
|  | 622.0 | .0234 |
|  | 636.0 | .0156 |
| HbCO | 535.0 | 1.2562 |
|  | 560.0 | 1.1220 |
|  | 577.0 | .9498 |
|  | 622.0 | .0303 |
|  | 636.0 | .0170 |
| SHb | 535.0 | .7549 |
|  | 560.0 | .7890 |
|  | 570.0 | .8138 |
|  | 622.0 | 2.3780 |
|  | 636.0 | .9596 |
| MetHb | 535.0 | .6573 |
|  | 560.0 | .4302 |
|  | 577.0 | .4187 |
|  | 622.0 | .3393 |
|  | 636.0 | .3259 |

(3) Using a matrix of 6 measurements and 6 equations, where, however, the non-normalized coefficients for turbidity are presumed to be equal:

| Derivative | λ | Coefficient |
|---|---|---|
| RHb | 535.0 | .8510 |
|  | 560.0 | 1.2080 |
|  | 577.0 | .8945 |
|  | 622.0 | .1203 |
|  | 636.0 | .0956 |
|  | 670.0 | .0679 |
| $HbO_2$ | 535.0 | 1.1427 |
|  | 560.0 | .7867 |
|  | 577.0 | 1.3424 |
|  | 622.0 | .0234 |
|  | 636.0 | .0156 |
|  | 670.0 | .0097 |
| HbCO | 535.0 | 1.2562 |
|  | 560.0 | 1.1220 |
|  | 577.0 | .9498 |
|  | 622.0 | .0303 |
|  | 636.0 | .0170 |
|  | 670.0 | .0053 |
| SHb | 535.0 | .7549 |
|  | 560.0 | .7890 |
|  | 570.0 | .8138 |
|  | 622.0 | 2.3780 |
|  | 636.0 | .9596 |
|  | 670.0 | .1457 |
| MetHb | 535.0 | .6573 |
|  | 560.0 | .4302 |
|  | 577.0 | .4187 |
|  | 622.0 | .3393 |
|  | 636.0 | .3259 |
|  | 670.0 | .0395 |
| Turb | 535.0 | .2420 |
|  | 560.0 | .2420 |
|  | 577.0 | .2420 |
|  | 622.0 | .2420 |
|  | 636.0 | .2420 |
|  | 670.0 | .2420 |

The results of the measurements appear from the Table below:

TABLE I

| | | Measuring result | | | |
|---|---|---|---|---|---|
| Sample | | tHb mmol/l | $HbO_2$SAT % | HbCO % | MetHb % |
| Calculation matrix of 6 × 6 according to the invention: | | | | | |
| A, | $HbO_2$ | 7.16 | 99.9 | 0.5 | 0.0 |
| B, | $HbO_2$ 95%:5% Intralipid ® | 7.69 | 100.6 | 1.7 | 0.3 |
| C, | $HbO_2$ 90%:10% Intralipid ® | 7.21 | 101.6 | 3.1 | 0.7 |
| D, | RHb | 8.36(7.9) | −0.3 | 0.9 | −0.3 |
| D, | RHb 95%:5% Intralipid ® | 7.86 | −0.6 | 1.4 | 0.0 |
| E, | RHb | 7.93(7.1) | −0.2 | 0.7 | −0.2 |
| E, | RHB 90%:10% Intralipid ® | 6.80 | −0.5 | −1.2 | −1.5 |
| Calculation matrix of 5 × 5: | | | | | |
| A, | $HbO_2$ | 7.19 | 99.8 | 0.3 | 0.4 |
| B, | $HbO_2$ 95%:5% Intralipid ® | 9.78 | 91.2 | −7.2 | 20.9 |
| C, | $HbO_2$ 90%:10% Intralipid ® | 12.91 | 78.3 | −16.1 | 43.3 |
| D, | RHb | 8.47(8.1) | −0.2 | 0.4 | 1.0 |
| D, | RHb 95%:5% Intralipid ® | 10.03 | 0.9 | −7.7 | 21.1 |
| E, | RHb | 8.04(7.2) | −0.1 | 0.1 | 1.1 |
| E, | RHb 90%:10% Intralipid ® | 15.60 | 4.2 | −23.4 | 54.2 |
| Calculation matrix of 6 × 6, but turbitidy presumed equal at all wavelengths: | | | | | |
| A, | $HbO_2$ | 7.17 | 99.9 | 0.5 | 0.1 |
| B, | $HbO_2$ 95%:5% Intralipid ® | 8.09 | 101.9 | 5.8 | 2.9 |
| C, | $HbO_2$ 90%:10% Intralipid ® | 8.31 | 105.6 | 13.8 | 7.7 |
| D, | RHb | 8.38(8.0) | −0.3 | 1.2 | −0.1 |
| D, | RHb 95%:5% Intralipid ® | 8.28 | −1.3 | 5.6 | 2.7 |
| E, | RHb | 7.95(7.2) | −0.2 | 0.9 | −0.1 |
| E, | RHb 90%:10% Intralipid ® | 8.50 | −4.1 | 15.7 | 9.4 |

(The corrected results for the undiluted samples are written in parentheses for the RHb-type.)

The results obtained with the partial turbidity compensation or no turbidity correction are totally unacceptable. For example, on the basis of the results for HbCO calculated with the partial turbidity correction one would expect that the patient were carbon monoxide poisoned.

EXAMPLE 2

A blood sample from a voluntary donor (healthy, non-smoker) was divided in three portions which were treated as follows:

One portion (A) was equilibrated for 0.5 hour with a gas mixture containing 4% of $CO_2$ and 96% of $O_2$ in a film tonometer. Thereafter, the portion was hemolyzed by addition of STEROX SE to a final concentration of 1%, and plasma phase constituting 10% of the total volume was added.

A minor part of the hemolyzed sample A (<250 μl) was injected into a scanning spectrophotometer (noncommercial type, made at Radiometer A/S, Copenhagen), the measuring cuvette of which corresponds to the cuvette of the apparatus according to the invention as described in connection with the drawing. A desk top computer of the type HP85 with attached plotter were connected to the spectrophotometer. As reference medium was used distilled water. The spectral absorptions were calculated by means of the HP85 and were plotted against the wavelengths range of 450–700 nm (curve A).

To another portion of the hemolyzed blood sample was added Intralipid ® [200 mg/ml of infusion liquid available from Kabi Vitrum A/S, Copenhagen (containing inter alia soy lecithin and glycerol)] up to a final concentration of 10% (v/v). The dilution was carried out in a Hamilton glass syringe. A portion of this mixture was injected into the spectrophotometer, and the absorption curve was made as described above (curve B1).

Finally, the spectrum for a sample consisting of the plasma phase from the same blood portion and 10% of Intralipid ® (final concentration 10% v/v) was determined (curve B2).

On the basis of the absorption data corresponding to curves 1 and 2 stored on tape in the HP85, the difference curve C (B1-B2) was calculated and plotted.

Figure 8:
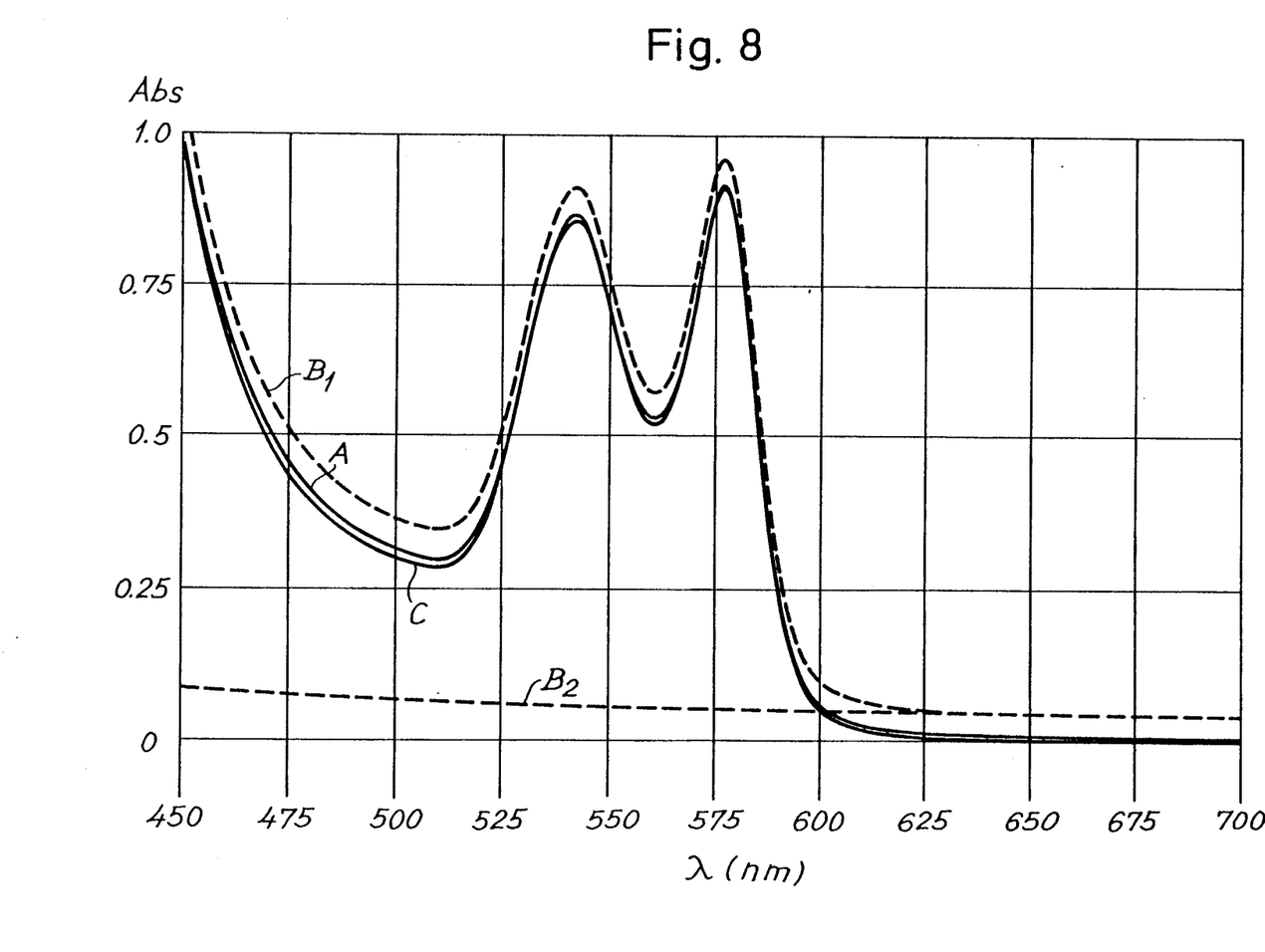
FIG. 8 is a diagram obtained by employing the measuring method according to the invention as explained in detail in Example 2.

The curves are shown in FIG. 8. It will be noted that the difference curve (curve C) and the curve for the turbidity-free sample (curve A) are almost identical.

We claim:

1. A method for spectrophotometrically determining the concentration of a number of hemoglobin derivatives comprising at least deoxyhemoglobin and oxyhemoglobin or parameters derived from the concentration of individual hemoglobin derivatives, including the oxygen saturation fraction, in whole blood, comprising
    transmitting light to the blood under test,
    determining the modification caused by the blood on the light transmitted to the blood at a number of individual wavelengths, wherein one of the individual wavelengths is above 535 nm and is a wavelength at which the ratio between absorption due to turbidity and absorption due to hemoglobin derivative is relatively high, and
    determining the concentrations or the derived parameters on the basis of the light modification at the individual wavelengths and on the basis of predetermined coefficients representing the light absorption characteristics of each of the hemoglobin derivatives at each of the individual wavelengths, any error on the determination values due to turbidity being substantially compensated for by utilizing predetermined coefficients representing an absorption characteristic of turbidity at each of the individual wavelengths.

2. The method of claim 1, wherein the wavelength is above 650 nm.

3. The method of claim 1, wherein the measurement is performed at a number of individual wavelengths which is at least equal to the number of hemoglobin derivatives to be determined plus one.

4. The method of claim 1, including determining the concentrations of any further components which modify the absorbance caused by the light transmitted to the blood sample at one or more of said individual wavelengths, or of the parameters derived from the concentrations of any of said further components, on the basis of said light absorbance modifications and on the basis of sets of predetermined coefficients for said further components applied to the measured absorbances of the blood sample at each said individual wavelength in an equation for the determination of the concentrations of said further components derived from the Lambert-Beer's Law; wherein each set of predetermined coefficients for said further components has been calculated using the Lambert-Beer's Law from the concentration and actual measured light absorbance of a known solution of each of said further components at each said individual wavelength, said individual hemoglobin derivatives, turbidity components and further components being treated as equivalent factors in the blood sample in deriving the foregoing equations for the determination of the concentrations of said further components, and in calculation of said coefficients for said further components.

5. The method of claim 4, wherein said further components comprise at least one diagnostic dyestuff selected from the group consisting of Evan's blue, Methylene Blue and Cardi Green, and/or at least one plasma pigment selected from the group consisting of bilirubin and carotene.

6. The method of claim 1, wherein the hemoglobin derivatives whose concentration is determined comprise deoxyhemoglobin, oxyhemoglobin, and at least one hemoglobin derivative selected from the group consisting of carboxyhemoglobin, methemoglobin and sulfhemoglobin.

7. The method of claim 1, wherein the light transmitted to the blood sample includes at least said individual wavelengths; and wherein the light, after absorbance modification by the blood sample is divided into components at least including said individual wavelengths.

8. A method for spectrophotometrically determining the concentration of a number of hemoglobin derivatives comprising at least deoxyhemoglobin and oxyhemoglobin or parameters derived from the concentration of individual hemoglobin derivatives, including the oxygen saturation fraction, in whole blood, comprising
    transmitting light to the blood under test,
    determining the modification caused by the blood on the light transmitted to the blood at a number of individual wavelengths, wherein the measurement is performed at a number of wavelengths which is at least equal to the number of hemoglobin derivatives to be determined plus one, and
    determining the concentrations or the derived parameters on the basis of the light modification at the individual wavelengths and on the basis of predetermined coefficients representing the light absorption characteristics of each of the hemoglobin derivatives at each of the individual wavelengths, any error on the determination values due to turbidity being substantially compensated for by utilizing predetermined coefficients representing an absorption characteristic of turbidity at each of the individual wavelengths.

9. The method of claim 8, wherein one of said individual wavelengths at which the absorbance modification caused by the blood on the light transmitted to the blood sample is determined at a wavelength above 650 nm at which the ratio between the absorbance due to the turbidity component and the absorbance due to said individual hemoglobin derivatives is relatively high.

10. The method of claim 9, including determining the concentrations of any further components which modify the absorbance caused by the light transmitted to the blood sample at one or more of said individual wavelengths, or of the parameters derived from the concentrations of any of said further components, on the basis of said light absorbance modifications and on the basis of sets of predetermined coefficients for said further components applied to the measured absorbances of the blood sample at each said individual wavelength in an equation for the determination of the concentrations of said further components derived from the Lambert-Beer's Law; wherein each set of predetermined coefficients for said further components has been calculated using the Lambert-Beer's Law from the concentration and actual measured light absorbance of a known solution of each of said further components at each said individual wavelength, said individual hemoglobin derivates, turbidity components and further components being treated as equivalent factors in the blood sample in deriving the foregoing equations for the determination of the concentrations of said further components, and in calculating said coefficients for said further components.

11. The method of claim 10, wherein said further components comprise at least one diagnostic dyestuff selected from the group consisting of Evan's blue, Methylene Blue and Cardio Green, and/or at least one plasma pigment selected from the group consisting of bilirubin and carotene.

12. The method of claim 8, wherein the hemoglobin derivatives whose concentration is determined comprise deoxyhemoglobin, oxyhemoglobin, and at least one hemoglobin derivative selected from the group consisting of carboxyhemoglobin, methemoglobin and sulfhemoglobin.

13. The method of claim 8, wherein the light transmitted to the blood sample includes at least said individual wavelengths; and wherein the light, after absorbance modification by the blood sample is divided into components at least including said individual wavelengths.

14. A method for spectrophotometrically determining the concentration of deoxyhemoglobin, oxyhemoglobin and one or several hemoglobin derivatives selected from carboxyhemoglobin, methemoglobin and sulfhemoglobin, in whole blood, comprising
  transmitting light to the blood under test,
  determining the modification caused by the blood on the light transmitted to the blood at a number of individual wavelengths, wherein the measurement is performed at a number of individual wavelengths, and
  determining the concentrations or the derived parameters on the basis of the light modification at the individual wavelengths and on the basis of predetermined coefficients representing the light absorption characteristics of each of the hemoglobin derivatives at each of the individual wavelengths, any error on the determination values due to turbidity being substantially compensated for by utilizing predetermined coefficients representing an absorption characteristic of turbidity at each of the individual wavelengths.

15. The method of claim 14, wherein one of said individual wavelengths at which the absorbance modification caused by the blood on the light transmitted to the blood sample is determined at a wavelength above 650 nm at which the ratio between the absorbance due to the turbidity component and the absorbance due to said individual hemoglobin derivatives is relatively high.

16. The method of claim 14, including determining the concentrations of any further components which modify the absorbance caused by the light transmitted to the blood sample at one or more of said individual wavelengths, or of the parameters derived from the concentrations of any of said further components, on the basis of said light absorbance modifications and on the basis of sets of predetermined coefficients for said further components applied to the measured absorbances of the blood sample at each said individual wavelength in an equation for the determination of the concentrations of said further components derived from the Lambert-Beer's Law; wherein each set of predetermined coefficients for said further components has been calculated using the Lambert-Beer's Law from the concentration and actual measured light absorbance of a known solution of each of said further components at each said individual wavelength, said individual hemoglobin derivatives, turbidity components and further components being treated as equivalent factors in the blood sample in deriving the foregoing equations for the determination of the concentrations of said further components, and in calculation of said coefficients for said further components.

17. The method of claim 16, wherein said further components comprise at least one diagnostic dyestuff selected from the group consisting of Evan's blue, Methylene Blue and Cardio Green, and/or at least one plasma pigment selected from the group consisting of bilirubin and carotene.

18. The method of claim 14, wherein the light transmitted to the blood sample includes at least said individual wavelengths; and wherein the light, after absorbance modification by the blood sample is divided into components at least including said individual wavelengths.

19. A method of spectrophotometrically determining the concentration of a number of individual hemoglobin derivatives comprising at least deoxyhemoglobin and oxyhemoglobin or parameters derived from the concentration of individual hemoglobin derivatives, including the oxygen saturation fraction, in whole blood, with substantial compensation for any error in the values of the individual concentrations or parameters caused by at least one turbidity component in the whole blood, comprising;
  (a) transmitting light to a blood sample which is under test;
  (b) determining the absorbance modification caused by the blood on the light transmitted to the blood sample at a number of individual wavelengths which are at least equal to the number of hemoglobin derivatives to be determined plus the number of turbidity components being compensated for;
  (c) determining the values of said individual hemoglobin derivative concentrations or of said parameters derived from said individual hemoglobin derivative concentrations on the basis of said light absorbance modifications and on the basis of sets of predetermined coefficients applied to the measured absorbances of the blood sample at each wavelength in an equation for the determination of the concentration of each of said derivatives derived from the Lambert-Beer's Law, wherein each set of predetermined coefficients has been calculated using the Lambert-Beer's Law from the concentration and actual measured light absorbance of a known solution of each individual hemoglobin derivative and turbidity component at each of said individual wavelengths, said individual hemoglobin derivatives and turbidity components being treated as equivalent factors in the blood sample in deriving the foregoing equations for the determination of the concentrations of said derivatives, and in calculating said coefficients.

20. The method of claim 19, wherein one of said individual wavelengths at which the absorbance modification caused by the blood on the light transmitted to the blood sample is determined at a wavelength above 650 nm at which the ratio between the absorbance due to the turbidity component and the absorbance due to said individual hemoglobin derivatives is relatively high.

21. The method of claim 19, including determining the concentrations of any further components which modify the absorbance caused by the light transmitted to the blood sample at one or more of said individual wavelengths, or of the parameters derived from the concentrations of any of said further components, on the basis of said light absorbance modifications and on the basis of sets of predetermined coefficients for said further components applied to the measured absorbances of the blood sample at each said individual wavelength in an equation for the determination of the concentrations of said further components derived from the Lambert-Beer's Law; wherein each set of predetermined coefficients for said further components has been calculated using the Lambert-Beer's Law from the concentration and actual measured light absorbance of a known solution of each of said further components at each said individual wavelength, said individual hemoglobin derivatives, turbidity components and further components being treated as equivalent factors in the blood sample in deriving the foregoing equations for the determination of the concentrations of said further components, and in calculation of said coefficients for said further components.

22. The method of claim 21, wherein said further components comprise at least one diagnostic dyestuff selected from the group consisting of Evan's blue, Methylene Blue and Cardio Green, and/or at least one plasma pigment selected from the group consisting of bilirubin and carotene.

23. The method of claim 19, wherein the hemoglobin derivatives whose concentration is determined comprise deoxyhemoglobin, oxyhemoglobin, and at least one hemoglobin derivative selected from the group consisting of carboxyhemoglobin, methemoglobin and sulfhemoglobin.

24. The method of claim 19, wherein the light transmitted to the blood sample includes at least said individual wavelengths; and wherein the light, after absorbance modification by the blood sample is divided into components at least including said individual wavelengths..

25. An apparatus for spectrophotometrically determining the concentration of a number of hemoglobin derivatives in a blood sample comprising at least deoxyhemoglobin and oxyhemoglobin or parameters derived from the concentration of individual hemoglobin derivatives in whole blood including the oxygen saturation fraction, said apparatus comprising
light source means for transmitting to the blood under test,
sample inlet means,
a conduit for conducting the blood sample from the sample inlet means through the apparatus, the conduit having transparent wall parts defining a light transmission path through a sample positioned in the conduit,
hemolyzing means for hemolyzing the blood sample in the conduit, said hemolyzing means including ultrasonic sound generation means, the light source means emitting light to the light transmission path,
light detector means for receiving light transmitted through the blood sample, and
measuring means for determining the modification of the transmitted light at a number of individual wavelengths and for determining the concentrations or the derived parameters on the basis of the modification of transmitted light measured at the individual wavelengths and on the basis of predetermined coefficients representing characteristics of the light absorption of each of the hemoglobin derivatives at each of the individual wavelengths,
said measuring means comprising computer means further including:
(i) storage means for storing data representing the predetermined coefficients of a number of hemoglobin derivatives at each of the individual wavelengths and for storing data representing the coefficients representing the absorption characteristic of turbidity at each of the individual wavelengths and
(ii) calculating means for calculating the oxygen saturation fraction, the hemoglobin derivative concentration or the derived parameters on the basis of the absorption of the blood sample measured at the individual wavelengths and the said data, ny error on the determinations due to turbidity being substantially compensated for by utilizing predetermined coefficients representing an absorption characteristic of turbidity at each of the individual wavelengths.

26. The apparatus of claim 25, wherein the light source means to adapted generate light including a plurality of wavelengths, and whrein the apparatus further comprises
means for dividing the light transmitted through the blood sample into individual components, at least including said individual wavelengths.

27. An apparatus for spectrophotometrically determining the concentration of a number of individual hemoglobin derivatives in a blood sample comprising at least deoxyhemoglobin and oxyhemoglobin or parameters derived from the concentration of individual hemoglobin derivatives, including the oxygen saturation fraction, in whole blood, with substantial compensation for any error in the values of the individual concentrations or parameters caused by at least one turbidity component in the whole blood, said apparatus comprising
(a) light source means for transmitting light to a blood sample which is under test;
(b) light detector means for receiving light modified by the blood sample; and
(c) measuring means for determining
(i) the absorbance modification caused by the blood on the light transmitted to the blood sample at a number of individual wavelengths which are at least equal to the number of hemoglobin derivatives to be determined plus the number of turbidity components being compensated for; and
(ii) the values of said individual hemoglobin derivative concentrations or of said parameters derived from said individual hemoglobin derivative concentrations on the basis of said light absorbance modifications and on the basis of sets of predetermined coefficients applied to the measured absorbances of the blood sample at each wavelength in an equation for the determination of the concentration of each of said derivatives derived from the Lambert-Beer's Law, wherein each set of predetermined coefficients has been calculated using the Lambert-Beer's Law from the concentration and actual measured light absorbance of a known solution of each individual hemoglobin derivative and turbidity component at each of said individual wavelengths, said individual hemoglobin derivatives and turbidity components being treated as equivalent factors in the blood sample in deriving the foregoing equations for the determination of the concentrations of said derivatives, and in calculating said coefficients.

28. The apparatus of claim 27, further comprising:
(d) sample inlet means
(e) a conduit for conducting the blood sample from the sample inlet means through the apparatus, the conduit having transparent wall parts defining a light transmission path through a sample positioned in the conduit, the light source means emitting light to the light transmission path and the light detector means for receiving light transmitted through the blood sample.

29. The apparatus of claim 28, wherein the measuring means comprises computer means further including:
(i) storage means for storing data representing the predetermined coefficients of a number of hemoglobin derivatives at each of the individual wavelengths and for storing data representing the coefficients representing the absorption characteristic of turbidity at each of the individual wavelengths, and
(ii) calculating means for calculating the oxygen saturation fraction, the hemoglobin derivative concentrations or the derived parameters on the basis of the absorbance of the blood sample measured at the individual wavelengths and the said data.

30. The apparatus of claim 27, wherein the light source means is adapted to generate light including a plurality of wavelengths, and wherein the apparatus further comprises
(f) means for dividing the light transmitted through the blood sample into individual components, at least including said individual wavelengths.

31. The apparatus of claim 27, further comprising
(g) hemolyzing means for the blood sample present within the conduit, including ultrasonic sound generator means.

* * * * *

UNITED STATES PATENT AND TRADEMARK OFFICE
CERTIFICATE OF CORRECTION

PATENT NO. : 4,997,769
DATED : March 5, 1991
INVENTOR(S) : FINN S. LUNDSGAARD

It is certified that error appears in the above-identified patent and that said Letters Patent is hereby corrected as shown below:

Column 5, line 60:   Change "glycerol)" to --glycerol))--.
Column 6, line 38:   Change "cMetH6" to --cMetHb--.
Column 6, line 47:   Change "-51.850" to --+51.850--.
Column 10, line 40:  Change "37°C." to --37°C--.
Column 19, line 5:   Change "were" to --was--.
Column 24, line 33, claim 42:  Change "ny" to --any--.
Column 24, line 41, claim 43:  Change "whrein" to --wherein--.
Column 26, line 5:   Change "claim 28" to --claim 27--.

Signed and Sealed this

Twenty-second Day of September, 1992

Attest:

DOUGLAS B. COMER

Attesting Officer

Acting Commissioner of Patents and Trademarks